United States Patent
Mandalam et al.

(10) Patent No.: US 10,676,714 B2
(45) Date of Patent: **\*Jun. 9, 2020**

(54) SUSPENSION CULTURE OF HUMAN EMBRYONIC STEM CELLS

(71) Applicant: Asterias Biotherapeutics, Inc., Fremont, CA (US)

(72) Inventors: Ramkumar Mandalam, Union City, CA (US); Yan Li, Tallahassee, FL (US); Isabelle Nadeau-Demers, San Francisco, CA (US)

(73) Assignee: Asterias Biotherapeutics, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/894,842

(22) Filed: Feb. 12, 2018

(65) Prior Publication Data

US 2019/0017014 A1     Jan. 17, 2019

Related U.S. Application Data

(63) Continuation of application No. 14/791,479, filed on Jul. 6, 2015, now abandoned, which is a continuation of application No. 11/917,993, filed as application No. PCT/US2006/023976 on Jun. 20, 2006, now Pat. No. 9,074,181.

(60) Provisional application No. 60/693,266, filed on Jun. 22, 2005.

(51) Int. Cl.
   *C12N 5/0735* (2010.01)

(52) U.S. Cl.
   CPC ...... *C12N 5/0606* (2013.01); *C12N 2501/115* (2013.01); *C12N 2501/125* (2013.01); *C12N 2501/15* (2013.01); *C12N 2501/26* (2013.01)

(58) Field of Classification Search
   CPC ............ C12N 5/0606; C12N 2501/115; C12N 2501/125; C12N 2501/15; C12N 2501/26
   See application file for complete search history.

(56) References Cited

U.S. PATENT DOCUMENTS

| | | |
|---|---|---|
| 5,166,065 A | 11/1992 | Williams |
| 5,332,672 A | 7/1994 | Conover et al. |
| 5,405,772 A | 4/1995 | Ponting |
| 5,453,357 A | 9/1995 | Hogan |
| 5,583,016 A | 12/1996 | Villeponteau et al. |
| 5,843,780 A | 12/1998 | Thomson |
| 5,914,268 A | 6/1999 | Keller et al. |
| 5,922,567 A | 7/1999 | Verfaillie et al. |
| 5,968,829 A | 10/1999 | Carpenter |
| 6,090,622 A | 7/2000 | Gearhart et al. |
| 6,200,806 B1 | 3/2001 | Thomson |
| 6,280,718 B1 | 8/2001 | Kaufman et al. |
| 6,458,589 B1 | 10/2002 | Rambhatla et al. |
| 6,576,464 B2 | 6/2003 | Gold et al. |
| 6,642,048 B2 | 11/2003 | Xu et al. |
| 6,800,480 B1 | 10/2004 | Bodnar et al. |
| 6,833,269 B2 | 12/2004 | Carpenter |
| 6,875,607 B1 | 4/2005 | Reubinoff et al. |
| 7,005,252 B1 | 2/2006 | Thomson |
| 7,041,438 B2 | 5/2006 | Carpenter et al. |
| 7,410,789 B2 | 8/2008 | Schlosser et al. |
| 7,413,904 B2 | 8/2008 | Gold et al. |
| 7,455,983 B2 | 11/2008 | Xu et al. |
| 7,473,555 B2 | 1/2009 | Mandalam et al. |
| 7,790,456 B2 | 9/2010 | Terstegge et al. |
| 9,074,181 B2 | 7/2015 | Mandalam et al. |
| 2002/0081724 A1 | 6/2002 | Carpenter et al. |
| 2003/0017589 A1 | 1/2003 | Mandalam et al. |
| 2003/0113910 A1 | 6/2003 | Levanduski |
| 2003/0153082 A1 | 8/2003 | Bhatia |
| 2005/0037492 A1 | 2/2005 | Xu et al. |
| 2005/0164377 A1 | 7/2005 | Miyabayashi et al. |
| 2005/0233446 A1 | 10/2005 | Parsons et al. |
| 2010/0144033 A1 | 6/2010 | Mandalam et al. |
| 2019/0017014 A1 | 1/2019 | Mandalam et al. |

FOREIGN PATENT DOCUMENTS

| | | |
|---|---|---|
| AU | 729377 | 2/2001 |
| EP | 695351 | 12/1999 |
| JP | 200117163 | 1/2001 |
| WO | 199407997 | 4/1994 |
| WO | 199721802 | 6/1997 |
| WO | 199747734 | 12/1997 |
| WO | 199830678 | 7/1998 |
| WO | 199830679 | 7/1998 |
| WO | 199843679 | 10/1998 |
| WO | 199920741 | 4/1999 |
| WO | 199942122 | 8/1999 |
| WO | 199943785 | 9/1999 |

(Continued)

OTHER PUBLICATIONS

Mered, B. et. al., "Cell Growth Optimization in Microcarrier Culture," In Vitro 16(10), 1980, pp. 859-865.
Mitsui, K. et. al., "The Homeoprotein Nanog is Required for Maintenance of Pluripotency in Mouse Epiblast and ES Cells," Cell 113, 2003, pp. 631-642.
Miyamoto, K. et. al., "Human Placenta Feeder Layers Support Undifferentiated Growth of Primate Embryonic Stem Cells," Stem Cells 22, 2004, pp. 433-440.
Nichols, J. et. al., "Derivation of Germline Competent Embryonic Stem Cells with a Combination of Interleukin-6 and Soluble Interleukin-6 Receptor," Exp. Cell Res. 215, 1994, pp. 237-239.
Nichols, J. et. al., "Establishment of Germ-Line-Competent Embryonic Stem (ES) Cells Using Differentiation Inhibiting Activity," Development 110, 1990, pp. 1341-1348.

(Continued)

*Primary Examiner* — Thaian N Ton
(74) *Attorney, Agent, or Firm* — Bass, Berry & Sims, PLC (57) ABSTRACT

This disclosure provides an improved system for culturing human embryonic stem cells. The cells are cultured in suspension so as to maximize the production capacity of the culture environment. The new culture system of this invention allows for bulk proliferation of hES cells in a more cost-effective manner, which facilitates commercial production of important products for use in human therapy.

11 Claims, 6 Drawing Sheets

(56) References Cited

FOREIGN PATENT DOCUMENTS

| WO | 00/17323 | 3/2000 |
|---|---|---|
| WO | 200151610 | 7/2001 |
| WO | 200151616 A2 | 7/2001 |
| WO | 200166697 | 9/2001 |
| WO | 200181549 | 11/2001 |
| WO | 2003000868 | 1/2003 |
| WO | 2003004605 | 1/2003 |
| WO | 2003006950 | 1/2003 |
| WO | 2003020920 | 3/2003 |
| WO | 2003038070 | 5/2003 |
| WO | 2003050249 | 6/2003 |
| WO | 2003050250 | 6/2003 |
| WO | 2003050251 | 6/2003 |
| WO | 2004007696 | 1/2004 |
| WO | 2004055155 | 7/2004 |
| WO | 2005033298 | 4/2005 |
| WO | 2005090558 | 9/2005 |
| WO | 2006027229 | 3/2006 |
| WO | 2006070370 | 7/2006 |
| WO | 2008004990 | 1/2008 |
| WO | 2008015682 | 2/2008 |

OTHER PUBLICATIONS

Oh, S. et. al., "Human Embryonic Stem Cells: Technological Challenges Towards Therapy," Clin. Exp. Pharmacol. Physiol. 33, 2006, pp. 489-495.
Ornitz, D. et. al., "Fibroblast Growth Factors," Genome Biol. 2(3), 2001, pp. 1-12.
Pease, S. et. al., "Isolation of Embryonic Stem (ES) Cells in Media Supplemented with Recombinant Leukemia Inhibitory Factor (LIF)," Dev. Biol. 141, 1990, pp. 344-352.
Pebay, A. et. al., "Essential Roles of Sphingosine-1-Phosphate and Platelet-Derived Growth Factor in the Maintenance of Human Embryonic Stem Cells," Stem Cells 23(10), 2005, pp. 1541-1548.
Pyle, A. et.al., "Neurotrophins Mediate Human Embryonic Stem Cell Survival," Nature Biotech. 24(3), 2006, pp. 344-350.
Reijo et. al., 2009, Differentiation, vol. 78, pp. 18-23.
Reubinoff, B. et. al., "Embryonic Stem Cells Lines from Human Blastocysts: Somatic Differentiation In Vitro," Nature Biotechnol. 18, 2000, pp. 399-404.
Richards, M. et. al., "Comparative Evaluation of Various Human Feeders for Prolonged Undifferentiated Growth of Human Embryonic Stem Cells," Stem Cells 21, 2003, pp. 546-556.
Richards, M. et. al., "Human Feeders Support Prolonged Undifferentiated Growth of Human Inner Cell Masses and Embryonic Stem Cells," Nature Biotechnol. 20, 2002, pp. 933-936.
Robertson, E., "Derivation and Maintenance of Embryonic Stem Cell Cultures," Meth. Mol. Biol. 75, 1997, pp. 173-184.
Rose, T. et. al., "Oncostatin M (OSM) Inhibits the Differentiation of Pluripotent Embryonic Stem Cells In Vitro," Cytokine 6, 1994, pp. 48-54.
Rosler, E et. al., "Long-Term Culture of Human Embryonic Stem Cells in Feeder-Free Conditions," Dev. Dyn. 229, 2004, pp. 259-274.
Sato, N. et.al., "Maintenance of Pluripotency in Human and Mouse Embryonic Stem Cells Through Activation of Wnt Signaling by a Pharmalogical GSK-3-Specific Inhibitor," Nat. Med. 10(1), 2004, pp. 55-63.
Schultz, T. et. al., "Differentiation of Human Embryonic Stem Cells to Dopaminergic Neurons in Serum-Free Suspension Culture," Stem Cells 22, 2004, pp. 1218-1238.
Shamblott, M. et. al., "Derivation of Pluripotent Stem Cells from Cultured Human Primordial Germ Cells," Proc. Natl. Acad. Sci. USA 95, 1998, pp. 13726-13731.
Shamblott, M. et. al., "Human Embryonic Germ Cell Derivatives Express a Broad Range of Developmentally Distinct Markers and Proliferate Extensively In Vitro," Proc. Natl. Acad. Sci. USA 98, 2001, pp. 113-118.
Smith, A. et. al., "Inhibition of Pluripotential Embryonic Stem Cell Differentiation by Purified Polypeptides," Nature 336, 1988, pp. 688-690.
Scottile, V. et. al., "In Vitro Osteogenic Differentiation of Human ES Cells," Cloning Stem Cells 5(2), 2003, pp. 149-155.
Stojkovic, M. et. al., "Derivation, Growth and Applications of Human Embryonic Stem Cells," Reproduction 128, 2004, pp. 259-267.
Stojkovic, P. et. al., "An Autogeneic Feeder Cell System That Efficiently Supports Growth of Undifferentiated Human Embryonic Stem Cells," Stem Cells 23, 2005, pp. 306-314.
Strelchenko, N. et. al., "Embryonic Stem Cells from Morula," Meth. Enzymol. 418, 2006, pp. 93-108.
Thomson, J. et. al., "Embryonic Stem Cell Lines Derived from Human Blastocysts," Science 282, 1998, pp. 1145-1147.
Thomson, J. et. al., "Isolation of a Primate Embryonic Stem Cell Line," Proc. Natl. Acad. Sci. USA 92, 1995, pp. 1844-7848.
Thomson, J. et. al., "Primate Embryonic Stem Cells," Curr. Top. Dev. Biol. 38, 1998, pp. 133-165.
Tsukada, H. et. al., "Acidic Fibroblast Growth Factor Promotes Hepatic Differentiation of Monkey Embryonic Stem Cells," In Vitro Cell Dev Biol Anim Mar.-Apr. 2006; 42(3-4), pp. 83-88.
Vallier, L. et. al., "Activin/Nodal and FGF Pathways Cooperate to Maintain Pluripotency of Human Embryonic Stem Cells," J. Cell Sci. 118(Pt. 19), 2005, pp. 4495-4509.
Vallier, L. et. al., "Nodal Inhibits Differentiation of Human Embryonic Stem Cells Along the Neuroectodermal Default Pathway," Dev. Biol. 275, 2004, pp. 403-421.
Vassilieva, S. et. al., "Establishment of SSEA-1- and Oct-4-Expressing Rat Embryonic Stem-Like Cell Lines and Effects of Cytokines of the IL-6 Family on Clonal Growth," Exp. Cell Res. 258(2), 2000, pp. 361-373.
Wang, G. et. al., "Noggin and bFGF Cooperate to Maintain the Pluripotency of Human Embryonic Stem Cells in the Absence of Feeder Layers," Biochem. Biophys. Res. Commun. 330(3), 2005, pp. 934-942.
Wang, Q. et. al., "Derivation and Growth Human Embryonic Stem Cells on Feeders," Stem Cells 23(9), 2005, pp. 1221-1227.
Williams, R. et. al., "Myeloid Leukaemia Inhibitory Factor Maintains the Developmental Potential of Embryonic Stem Cells," Nature 336, 1988, pp. 684-687.
Xu, C. et. al., "Basic Fibroblast Growth Factor Supports Undifferentiated Human Embryonic Stem Cell Growth without Conditioned Medium," Stem Cells 23(3), 2005, pp. 315-323.
Xu, C. et. al., "Characterization and Enrichment of Cardiomyocytes Derived from Human Embryonic Stem Cells," Circ. Res. 91(6), 2002, pp. 501-508.
Xu, C. et. al., "Feeder-Free Growth of Undifferentiated Human Embryonic Stem Cells," Nature Biotech. 19, 2001, pp. 971-974.
Xu, C. et. al., "Immortalized Fibroblast-Like Cells Derived from Human Embryonic Stem Cells Support Undifferentiated Cell Growth," Stem Cells 22, 2004, pp. 972-980.
Xu, R. et. al. "Basic FGF and Suppression of BMP Signaling Sustain Undifferentiated Proliferation of Human ES Cells," Nat. Methods 2(3), 2005, pp. 185-190.
Yan et. al., "Single-Cell RNA-Seq Profiling of Human Preimplantation Embryos and Embryonic Stem Cells," Nature Structural & Molecular Biology 20(9), 2013, pp. 1131-1139.
Zandstra, P. et. al., "Leukemia Inhibitory Factor (LIF) Concentration Modulates Embryonic Stem Cell Self-Renewal and Differentiation Independently of Proliferation," Biotechnol. Bioeng. 69(6), 2000, pp. 607-617.
Zwaka, T., "Genetic Modification of Human Embryonic Stem Cells," in: Embryonic Stem Cells, Masters et. al., Eds., Springer, 2007, pp. 41-52.
Guo et. al., Stem Cell Reports, 6, 2016, pp. 437-446.
Dr. Lyle Armstrong to the UK House of Parliaments' Select Committee on Science and Technology, Fifth Report of Session 2006-2007, vol. II, Apr. 5, 2007, pp. 76-77.
Lai et. al., Proc Natl Acad Sci USA, 109(10), Mar. 6, 2012, pp. 3772-3777.
Dominguez-Bendala et. al., Handbook of Stem Cells, Chapter 70: Islet Cell Therapy and Pancreatic Stem Cells, 2013, pp. 835-853.

(56) References Cited

OTHER PUBLICATIONS

"Biographical Information for Dr. Andrea Bodnar," Bermuda Institute of Ocean Sciences webpage, 2011, 1 page.
"Biographical Information for Dr. James Thomson," University of Wisconsin-Madison webpage, 2011, 1 page.
"Biographical Information for Dr. Joseph Itskovitz-Eldor," Rambam Medical Center webpage, 2011, 1 page.
"Biographical Information for Dr. Peter Gray," University of Queensland webpage, 2011, 1 page.
Cole Palmer Catalog (2014) Available online at http://www.colepalmer.com/Product/Corning-roller-bottle-850-cm2-easy-grip- -cap/UX-0.
Al-Obeidi, F. et. al., "Development of Inhibitors for Protein Tyrosine Kinases," Oncogene 19, 2000, pp. 5690-5701.
Amit, M. et. al., "Clonally Derived Human Embryonic Stem Cell Lines Maintain Pluripotency and Proliferative Potential for Prolonged Periods of Culture," Dev. Biol. 227, 2000, pp. 271-280.
Amit, M. et. al., "Feeder Layer- and Serum-Free Culture of Human Embyronic Stem Cells," Biol. Reprod. 70, 2004, pp. 837-845.
Amit, M. et. al., "Human Feeder Layers for Human Embryonic Stem Cells," Biol. Reprod. 68, 2003, pp. 2150-2156.
Anzai, H. et. al., "Self-Renewal and Differentiation of a Basic Fibroblast Growth Factor-Dependent Multipotent Hematopoietic Cell Line Derived from Embryonic Stem Cells," Develop. Growth Differ. 41, 1999, pp. 51-58.
Baribault, H. et. al., "Embryonic Stem Cell Culture and Gene Targeting in Transgenic Mice," Mol. Biol. Med 6, 1989, pp. 481-492.
Beattie, G. et. al., "Activin A Maintains Pluripotency of Human Embryonic Stem Cells in the Absence of Feeder Layers," Stem Cells 23, 2005, pp. 485-495.
Berger, C. et. al., "Self Renewal of Embryonic Stem Cells in the Absence of Feeder Cells and Exongenous Leukemia Inhibitory Factor," Growth Factors 14, 1997, pp. 145-159.
Brook, F. et. al., "The Origin and Efficient Derivation of Embryonic Stem Cells in the Mouse," Proc. Natl. Acad. Sci USA 94, 1997, pp. 5709-5712.
Carpenter, M. et. al., "Properties of Four Human Embryonic Stem Cell Lines Maintained in a Feeder-Free Culture System," Dev. Dyn. 229(2), 2004, pp. 243-258.
Chambers, I, et. al., "Functional Expression Cloning of Nanog, a Pluripotency Sustaining Factor in Embryonic Stem Cells," Cell 113, 2003, pp. 643-655.
Cheng, L. et. al. "Human Adult Marrow Cells Support Prolonged Expansion of Human Embryonic Stem Cells in Culture," Stem Cells 21, 2003, pp. 131-142.
Coutu, D. L. et. al., "Roles of FGF Signaling in Stem Cell Self-Renewal, Senescence and Aging," Aging, 3(10), 2001, pp. 920-933.
Dang, S. et. al., "Controlled, Scalable Embryonic Stem Cell Differentiation Culture," Stem Cells 22(3), 2004, pp. 275-282.
Darden, T. et. al., "Selected New Developments in Computational Chemistry," Environ. Health Perspectives 104(Suppl. 1), 1996, pp. 69-74.
Denning, C. et. al., "Common Culture Conditions for Maintenance and Cardiomyocyte Differentiation of the Human Embryonic Stem Cell Lines," BG01 and HUES-7, Int. J. Dev. Biol. 50(1), 2006, pp. 27-37.
Denville Scientific, 1-2, accessed online at http://www.denvillescientific.com/node/4662 on May 6, 2014.
Dravid, G. et. al., "Defining the Role of Wnt-Catenin Signaling in the Survival, Proliferation and Self-Renewal of Human Embryonic Stem Cells," Stem Cells 23(10), 2005, pp. 1489-1501.
Drukker, M. et. al., "Genetic Manipulation of Human Embryonic Stem Cells," Human Embryonic Stem Cells, Chiu & Rao, Eds., Humana Press, Inc., Totowa, NJ, 2003, pp. 265-284.
Dvorak, P. et. al., "Expression and Potential Role of Fibroblast Growth Factor 2 and Its Receptors in Human Embryonic Stem Cells," Stem Cells 23(8), 2005, pp. 1200-1211.

Eiges, R. et. al., "Establishment of Human Embryonic Stem Cell-Transfected Clones Carrying a Marker for Undifferentiated Cells," Curr. Biol. 11(7), 2001, pp. 514-518.
Evans, M. et. al., "Establishment in Culture of Pluripotential Cell from Mouse Embryos," Nature 292, 1981, pp. 154-156.
Fok, E. et. al., "Shear-Controlled Single-Step Mouse Embryonic Stem Cell Expansion and Embryoid Body-Based Differentiation," Stem Cells 23(9), 2005, pp. 1333-1342.
Genbacev, O. et. al., "Serum-Free Derivation of Human Embryonic Stem Cell Lines on Human Placental Fibroblast Feeders," Fertil. Steril. 83(5), 2005, pp. 1517-1529.
Gendall, A. et. al., "Isolation and Characterization of Leukemia Inhibitory Factor-Independent Embryonic Stem Cell Line," Int. J. Biochem. Cell. Biol. 29(5), 1997, pp. 829-840.
Gerecht-Nir, S. et. al., "Bioreactor Cultivation Enhances the Efficiency of Human Embryoid Body (hEB) Formation and Differentiation," Biotechnol. Bioeng. 86(5), 2004, pp. 493-502.
Hovatta, O. et. al., "A Culture System Using Human Foreskin Fibroblasts as Feeder Cells Allows Production of Human Embryonic Stem Cells," Hum. Reprod. 18, 2003, pp. 1404-1409.
Invitrogen, "Invitrogen web pages re Lipofectamine 2000," 2010, 6 pages.
Itskovitz-Eldor, J. et. al., "Differentiation of Human Embryonic Stem Cells Into Embryoid Bodies Comprising the Three Embryonic Germ Layers," Mol. Med. 6(2), 2000, pp. 88-95.
James, D. et. al., "TGF/Activin/Nodal Signaling is Necessary for the Maintenance of Pluripotency in Human Embryonic Stem Cells," Development 132(6), 2005, pp. 1273-1282.
Kehat, I. et. al., "Human Embryonic Stem Cells Can Differentiate Into Myocytes with Structural and Functional roperties of Cardiomycytes," J. Clin. Invest. 108(3), 2001, pp. 407-414.
Kehoe, D. et. al., "Scalable Stirred-Suspension Bioreactor Culture of Human Pluripotent Stem Cells," Tissue Eng. 16(2), Part A, 2010, pp. 405-421.
Keirstead, H. et. al., "Human Embryonic Stem Cell-Derived Oligodendrocyte Progenitor Cell Transplants Remyelinate and Restore Locomotion After Spinal Cord Injury," J. Neurosci. 25(19), 2005, pp. 4694-4705.
Keller, G., "In Vitro Differentiation of Embryonic Stem Cells," Curr. Opin. Cell Biol. 7(6), 1995, pp. 862-869.
Klimanskaya, I. et. al., "Human Embryonic Stem Cells Derived without Feeder Cells," Lancet 365(9471), 2005, pp. 1636-1641.
Koshimizu, U. et. al., "Functional Requirement of gp130-Mediated Signaling for Growth and Survival of Mouse Primordial Germ Cells In Vitro and Derivation of Embryonic Germ (EG) Cells," Development 122, 1996, pp. 1235-1242.
Koshimizu, U. et. al., "Rapid Communication Retinoic Acid is a Potent Growth Activator of Mouse Primordial Germ Cells In Vitro," Dev. Biol. 168, 1995, pp. 683-685.
Kurosawa, H., "Methods for Inducing Embryoid Body Formation: In Vitro Differentiation System of Embryonic Stem Cells," J. Biosci. Bioeng. 103(5), 2007, pp. 389-398.
Lebkowski, J. et. al., "Human Embryonic Stem Cells: Culture Differentiation, and Genetic Modification for Regenerative Medicine Applications," Cancer J. (Suppl. 2), 2001, S83-S94.
Levenstein, M. et. al., "Basic FGF Support of Human Embryonic Stem Cell Self-Renewal," Stem Cells 24(3), 2006, pp. 568-574.
Li, Y. et. al., "Expansion of Human Embryonic Stem Cells in Defined Serum-Free Medium Devoid of Animal-Derived Products," Biotechnol. Bioeng. 91(6), 2005, pp. 688-698.
Lim, J. et. al., "Proteosome Analysis of Conditioned Medium from Mouse Embryonic Fibroblast Feeder Layers which Support the Growth of Human Embryonic Stem Cells," Proteomics 2, 2002, pp. 1187-1203.
Ludwig, T. et. al., "Derivation of Human Embryonic Stem Cells in Defined Conditions," Nat. Biotechnol. 24(2), 2006, pp. 185-187.
Matsuda, T. et. al., "STAT3 Activation is Sufficient to Maintain an Undifferentiated State of Mouse Embryonic Stem Cells," EMBO J. 18, 1999, pp. 4261-4269.
Matsui, Y. et. al., "Derication of Pluripotential Embryonic Stem Cells from Murine Primordial Germ Cells in Culture," Cell 70, 1992, pp. 841-847.

(56) References Cited

OTHER PUBLICATIONS

Xiao, et al., "Activin A Maintains Self-Renewal and Regulates Fibroblast Growth Factor, Wnt, and Bone Morphogenic Protein Pathways in Human Embryonic Stem Cells", Stem Cells, Embryonic Stem Cells: Characterization Series, 2006, pp. 1476-1486.

SUSPENSION CULTURE OF HUMAN EMBRYONIC STEM CELLS

REFERENCE TO RELATED APPLICATIONS

This application is a continuation of application Ser. No. 14/791,479, filed Jul. 06, 2015 (now abandoned), which is a continuation of application Ser. No. 11/917,993, filed Mar. 04, 2008 (now U.S. Pat. No. 9,074,181), which is the National Stage of International Application No. PCT/US2006/023976, filed Jun. 20, 2006, which claims the benefit of Provisional Application No. 60/693,266, filed Jun. 22, 2005. All of the above-identified applications are hereby incorporated by reference in their entirety.

BACKGROUND

Regenerative medicine is benefiting from recent advances relating to the isolation, culture, and use of various types of progenitor cells. This disclosure provides further improvements for the commercial development of human pluripotent stem cells and their derivatives.

Embryonic stem cells have two very special properties: First, unlike other normal mammalian cell types, they can be propagated in culture almost indefinitely, providing a virtually unlimited supply. Second, they can be used to generate a variety of tissue types of interest as a source of replacement cells and tissues for use in tissue therapy, or for use in the screening of pharmaceutical agents.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090,622). Both hES and hEG cells have the long-sought characteristics of pluripotent stem cells: they can be cultured extensively without differentiating, they have a normal karyotype, and they are capable of producing a number of important cell types.

A significant challenge to the use of pluripotent stem cells for therapy is that they are traditionally cultured on a layer of feeder cells to prevent differentiation (U.S. Pat. No. 5,843,780; U.S. Pat. No. 6,090,622). According to Thomson et al. (Science 282:114, 1998), hPS cells cultured without feeders soon die, or differentiate into a heterogeneous population of committed cells. Leukemia inhibitory factor (LIF) inhibits differentiation of mouse ES cells, but it does not replace the role of feeder cells in preventing differentiation of human ES cells.

U.S. Pat. No. 6,800,480 (Geron Corp.) is entitled Methods and materials for the growth of primate-derived primordial stem cells. International Patent Publication WO 01/51616 (Geron Corp.) is entitled Techniques for growth and differentiation of human pluripotent stem cells. An article by Xu et al. (Nature Biotechnology 19:971, 2001) is entitled *Feeder-free growth of undifferentiated human embryonic stem cells*. An article by Lebkowski et al. (Cancer J. 7 Suppl. 2:S83, 2001) is entitled *Human embryonic stem cells: culture, differentiation, and genetic modification for regenerative medicine applications*. International Patent Publication WO 03/020920 is entitled Culture System for Rapid Expansion of Human Embryonic Stem Cells. An article by Li et al. (Biotechnology and Bioengineering, Published Online: 21 Jun. 2005) is entitled *Expansion of human embryonic stem cells*. These publications report exemplary culture reagents and techniques for propagating embryonic stem cells in an undifferentiated state, and their use in preparing cells for human therapy.

The information provided in the section below further advances the science of hES cell culture that will facilitate growing and manipulating undifferentiated pluripotent stem cells, and help realize the full commercial potential of embryonic cell therapy.

SUMMARY OF THE INVENTION

This disclosure provides an improved system for culturing and proliferating primate pluripotent stem (hES) cells. The suspension culture system of this invention enables the user to produce high-quality embryonic stem cells in a rapid and volume-efficient mode, for use in therapy and drug discovery.

One aspect of this invention is a culture of human embryonic stem (hES) cells in suspension, wherein the hES cells are substantially undifferentiated. The culture may contain one or more of the following: fibroblast growth factor at a high concentration, other medium additives such as TGFβ, stem cell factor (SCF), or Flt3 ligand (Flt3L), one or more soluble or suspended extracellular matrix components such as laminin and/or fibronectin, or solid microparticles of various kinds, optionally porous in nature or coated with extracellular matrix.

Another aspect of the invention is a method for culturing hES cells, comprising: suspending the cells in a nutrient medium; maintaining the cells in suspension while culturing in a system such as described above; changing the medium periodically; optionally splitting the culture from time to time so as to reduce cell density; and finally harvesting cells from the culture.

Another aspect of this invention is a system or kit for culturing hES cells in suspension, comprising one or more of the components already referred to, or described below.

These and other aspects of the invention will be apparent from the description that follows.

DETAILED DESCRIPTION

Previous technology for growing primate pluripotent stem (hES) cells has involved culturing on a solid surface: either fibroblast feeder cells (U.S. Pat. No. 6,200,806), or extracellular matrix (U.S. Pat. No. 6,800,480). The feeder-free technology can be optimized to allow for rapid expansion WO 03/020920, substantially reducing the cost of hES cell production for commercial purposes.

The information disclosed below provides a new system that further advances the art of hES cell culture. Specifically, the production capacity of the culture is no longer constrained by the two dimensional size of the culture surface, and makes fuller use of the three-dimensions of the entire culture vessel. Growth conditions have been identified that permit hES cells to be cultured in suspension for over three months (Example 4). hES cells cultured in suspension maintain phenotypic characteristics of undifferentiated cells, and maintain the full potential to differentiate into tissue types representing any of the three germ layers (Example 3).

The ability to culture hES cells in a three-dimensional space should make the bulking up of hES cells an even more cost-effective process, and provides further opportunities to optimize the production capacity and growth rate of hES cell cultures. The use of suspension cultures also facilitates the adaptation of hES cell culture methods to a closed system, where cells and media are introduced and recovered from the system in a sterile manner, but the system can otherwise be handled in a less scrupulous environment.

Further advantages of the invention will be understood from the sections that follow.

Definitions

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells having markers for tissue types of all three germ layers in culture.

Included in the definition of pPS cells are embryonic cells of various types, exemplified by hES cells, defined below; embryonic stem cells from other primates, such as Rhesus or marmoset stem cells (Thomson et al., Proc. Natl. Acad. Sci. USA 92:7844, 1995; Developmental Biology 38:133, 1998); and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

Prototype "human Embryonic Stem cells" (hES cells) are described by Thomson et al. (Science 282:1145, 1998; U.S. Pat. No. 6,200,806). The scope of the term covers pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

hES cell cultures are described as "undifferentiated" when a substantial proportion of stem cells and their derivatives in the population display morphological characteristics of undifferentiated cells, clearly distinguishing them from differentiated cells of embryo or adult origin. Undifferentiated hES cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated hES cells on an ongoing basis, and may contain at least 40%, 60%, or 80% in order of increasing preference (in terms percentage of cells with the same genotype that are undifferentiated).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

A "nutrient medium" is a medium for culturing cells containing nutrients that promote proliferation. The nutrient medium typically contains isotonic saline, buffer, a protein source (in the form of one or more added proteins or amino acids), and potentially other exogenously added nutrients and growth factors.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

A "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

General Techniques

General methods in molecular genetics and genetic engineering are described in the current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found in Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other references of interest include Culture Is Our Business (M. McLuhan, Ballantine Books, 1970); and Understanding Media (M. McLuhan, Signet, 1970). Tissue culture supplies and reagents are available from commercial vendors such as Gibco/BRL, Nalgene-Nunc International, Sigma Chemical Co., and ICN Biomedicals.

Sources of Stem Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using primary mouse fibroblast feeder cells, according to the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. hES cell lines can also be derived on human feeders (U.S. Pat. No. 6,642,048), or in conditions entirely free of feeder cells (US 2002/0081724 A1). Equivalent cell types to hES cells include their pluripotent derivatives, such as primitive ectoderm-like (EPL) cells, as outlined in WO 01/51610 (Bresagen).

The illustrations provided in the Example section ensue from work done with hES cells. However, except where otherwise required, the invention can be practiced using other cells that meet the definition of primate pluripotent stem cells.

By no means does the practice of this invention require that a human blastocyst be disaggregated in order to produce the hES or embryonic stem cells for practice of this invention. hES cells can be obtained from established lines obtainable from public depositories (for example, the WiCell Research institute, Madison Wis. U.S.A., or the American Type Culture Collection, Manassas Va., U.S.A.). Human Embryonic Germ (hEG) cells can be prepared from primordial germ cells as described in Shamblott et al., Proc. Natl. Acad. Sci. U.S.A. 95:13726, 1998 and U.S. Pat. No. 6,090,622. U.S. Patent Publication 2003/0113910 A1 reports pluripotent stem cells derived without the use of embryos or fetal tissue. It may also be possible to reprogram other progenitor cells into hES cells by using a factor that induces the pluripotent phenotype (Chambers et al., Cell 113:643, 2003; Mitsui et al., Cell 113:631, 2003). Under appropriate conditions, any cell with appropriate proliferative and differentiation capacities can be used for the derivation of differentiated tissues for use according to this invention.

Propagation of hES Cells

Initially, most scientists in the field preferred to culture hES cells a layer of feeder cells to prevent differentiation, as originally described by Thomson (U.S. Pat. No. 5,843,780; U.S. Pat. No. 6,090,622).

Early on, scientists at Geron discovered culture systems in which the elements contributed by the 15 feeder cells to promote proliferation of the undifferentiated phenotype could be provided in another form. U.S. Pat. No. 6,800,480, WO 01/51616 (Geron Corp.), and Xu et al. (Nature Biotechnology 19:971, 2001) describe a feeder-free culture environment that supports proliferation without differentiation.

One aspect of the feeder-free culture method is to support the hES cells by culturing on an extracellular matrix. The matrix can be deposited by preculturing and lysing a matrix-forming cell line (U.S. Pat. No. 6,800,480), such as the STO mouse fibroblast line (ATCC Accession No. CRL-1503), or human placental fibroblasts. The matrix can also be coated directly into the culture vessel with isolated matrix components. Matrigel® is a soluble preparation from Engelbreth-Holm-Swarm tumor cells that gels at room temperature to form a reconstituted basement membrane. Other suitable extracellular matrix components may include laminin, fibronectin, proteoglycan, vitronectin, entactin, heparan sulfate, and so on, alone or in various combinations. The matrix components may be human, and/or produced by recombinant expression. Substrates that can be tested using the experimental procedures described herein include not only other extracellular matrix components, but also polyamines, hydrogels, and other commercially available coatings.

Another aspect of the feeder-free culture system is the nutrient medium. The medium will generally contain the usual components to enhance cell survival, including isotonic buffer (i.e., a buffer that is isotonic when adjusted to working concentration), essential minerals, and either serum or a serum replacement of some kind.

A direct way to introduce hES supportive factors is to precondition the medium with primary mouse embryonic fibroblasts (mEF) which can be prepared as described in U.S. Pat. No. 6,200,806 or WO 01/51616. Also suitable as feeder cells are telomerized cell lines, and human cell lines obtained from differentiating hES cells (U.S. Pat. No. 6,642,048) or other primitive cell types. hES cell medium can be conditioned by culturing the feeder cells (typically irradiated or otherwise inactivated). Medium conditioned by culturing for 1-2 hours at 37° C. contains a concentration of factors that support hES cell culture for about 1-2 days. However, the conditioning period can be adjusted upwards or downwards, determining empirically what constitutes an adequate period.

As an alternative to conditioned medium, hES cells can be grown in fresh (non-conditioned) medium containing added factors that invoke the appropriate signal transduction pathways in undifferentiated cells. A suitable base medium for use without conditioning can be identified empirically. The medium typically contains a neutral buffer (such as phosphate and/or high concentration bicarbonate) in isotonic solution; a protein nutrient (e.g., serum such as FBS, serum replacement, albumin, or essential and non-essential amino acids such as glutamine). It also typically contains lipids (fatty acids, cholesterol, an HDL or LDL extract of serum) and other ingredients found in most stock media of this kind (such as insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

Many suitable commercially available base media have been developed for culturing proliferative cell types like hematopoietic cells. Exemplary are X-VIVO™ 10 expansion medium (Biowhittaker) and QBSF™-60 (Quality Biological Inc.) (Example 1). See also WO 98/30679 (Life Technologies Inc.) and U.S. Pat. No. 5,405,772 (Amgen). The X-VIVO™ 10 formulation contains pharmaceutical grade human albumin, recombinant human insulin and pasteurized human transferrin. Exogenous growth factors, artificial stimulators of cellular proliferation or undefined supplements are not included in the X-VIVO™ 10 medium. They are also devoid of any protein-kinase C stimulators. QBSF™-60 is a serum-free formulation that contains recombinant or pasteurized human proteins. Other potential alternatives are Ex-Cell VPRO™ medium made by JRH Biosciences, and HyQ CDM4™ made by Hyclone.

The base medium is supplemented with additives that promote proliferation of the undifferentiated phenotype while inhibiting differentiation. Fibroblast growth factor at high concentration is especially effective to promote hES cell proliferation without differentiation. Exemplary are basic FGF (FGF-2), and FGF-4, but other members of the family can also be used. Equivalent forms are species homologs, artificial analogs, antibodies to the respective FGF receptor, and other receptor activating molecules. It has been determined from gene expression analysis that undifferentiated hES cells express receptors for acidic FGF (FGF-1). At a high concentration, FGF alone is sufficient to promote growth of hES cells in an undifferentiated state (Examples 1 and 2). Concentrations of FGF effective for promoting undifferentiated hES cell growth on their own usually have a lower bound of about 20, 30, or 40 ng/mL, with a practical upper bound of about 200, 500, or 1000 ng/mL. Concentrations of at least 60, 80, or 100 ng/mL bFGF are both reliable and cost effective. Equivalent concentrations of other forms and analogs of FGF can be determined empirically by weaning cultures from bFGF into the proposed substitute, and monitoring the culture for differentiation according to the marker system described below.

Culturing hES Cells in Suspension

It has now been discovered that hES cells can be grown in suspension culture, rather than letting the cells grow on a solid substrate.

hES cells expanded by another culture method (or obtained from a primary source) are inoculated into a vessel adapted to keep the cells in suspension. The vessel walls are typically inert or resistant to adherence of undifferentiated hES cells. There is also a means for preventing the cells from settling out, such as a stirring mechanism like a magnetically or mechanically driven stir bar or paddle, a shaking mechanism (typically attached to the vessel by the outside), or an inverting mechanism (i.e., a device that rotates the vessel so as to change the direction of gravity upon the cells).

Vessels suitable for suspension culture for process development include the usual range of commercially available spinner or shaker flasks. Fermentors suitable for commercial production are Celligen Plus (New Brunswick Scientific Co.) and the Stirred-Tank Reactor™ (Applikon Inc.). These bioreactors can be continuously perfused with medium or used in a fed-batch mode, and come in various sizes.

Nutrient medium that helps maintain the undifferentiated phenotype and supports growth is replaced as needed (for example, by letting the cells settle out, replacing the medium, and then resuspending the cells). Growth is monitored, and the culture is split when required to make room for further growth. After a suitable culture period, the cells are harvested and used for their intended purpose.

Media and other components designed for growing hES cells in the absence of feeders on a solid surface may also work in suspension cultures. Either conditioned or fresh media can be used (Example 4). However, the dynamics of suspension culture provide the user with a further opportunity to optimize the various components of the culture system. Without intending to be limited by theory, it is a hypothesis of this invention that suspension culture will be enhanced if the hES cells are permitted to form small undifferentiated clusters (the three-dimensional equivalent of an undifferentiated colony on a solid surface), possibly surrounded by cells partly differentiated into stromal cells—or if the hES cells are dispersed, but shielded from the dynamic fluid forces that otherwise might cause differentiation.

Optimization of the suspension culture system can be accomplished by empirical testing. Undifferentiated cells from a previous surface or suspension culture are passaged to the test condition, and cultured for a week or more. The cells can be examined periodically for characteristics of hES cells, for example, using the marker system described in the next section, and illustrated in Example 1. The cells can also be passaged back to a well-established culture system, and evaluated for classic morphological features of undifferentiated cells (Example 3). If the hES cells are intended ultimately for differentiation into a particular tissue type, then the ultimate test may not be the marker profile of the undifferentiated culture, but the ability of the cells to differentiate as required. The pluripotency of hES suspension cultures can be confirmed by sampling the cells, and either producing teratomas in SCID mice, or by staining EB-derived cells for markers representing all three germ layers (Example 3). The user can thereby optimize the system to achieve a high growth rate while retaining the full pluripotency of the cells (or at least the ability of the cells to differentiate into the intended tissue of interest).

Aspects of the culture system that may benefit from further optimization include the nutrient medium. Alternative base media and alternative FGF additives are listed in the previous section. It may also be advantageous to use one or more additional additives, such as the following:

stem cell factor (SCF, Steel factor), other ligands or antibodies that dimerize c-kit, and other activators of the same signal transduction pathway     ligands for other tyrosine kinase related receptors, such as the receptor for platelet-derived growth factor (PDGF), macrophage colony-stimulating factor, Flt-3 ligand and vascular endothelial growth factor (VEGF)

factors that elevate cyclic AMP levels, such as forskolin     factors that induce gp130, such as LIF or Oncostatin-M;

hematopoietic growth factors, such as thrombopoietin (TPO)

transforming growth factors, such as TGFβ1 other growth factors, such as epidermal growth factor (EGF)

neurotrophins, such as CNTF

With a view to protecting the cells from adhering to each other, adhering to the vessel wall, or forming clusters that are too big, it may be beneficial to include an anti-clumping agent, such as those sold by Invitrogen (Cat #0010057AE).

While the cells have some capacity to form their own extracellular matrix to a limited extent, it may also be beneficial to include one or more extracellular matrix components either dissolved or suspended in the medium. A suitable working range to keep laminin in suspension is about 10 to 33 µg/mL. Other candidate matrix components for suspension cultures include some of those listed earlier, particularly fibronectin, proteoglycan, vitronectin, and artificial equivalents thereof. The extracellular matrix may assist the cells in forming small aggregates of an appropriate size.

Alternatively or in addition, the suspension culture may contain particulate carriers that create surfaces within the suspension, but still provide the benefits of culturing the cells in a three-dimensional space. The cells are cultured and passaged in the same way, except that the particles are retained in the vessel during medium exchange, and more particles are added when the cells are split.

One type of microcarrier is solid spherical or semi-spherical particles made from glass, plastic, dextran having a positive charge to augment cell attachment (Cytodex), and so on. Another type is disk-shaped culture plastic, such as the Fibra-cel Disks™ sold by New Brunswick Scientific Co, Inc. A gram of these disks provide a surface area of 1200 cm$^2$. Solid carriers are optionally coated with an hES cell friendly extracellular matrix, such as laminin, so that the attached cells have the same microenvironment as cells plated onto a solid surface.

Another type of microcarrier is macroporous particles of various pore sizes that permit the cells to reside in the interior as well as the outside, to potentially enhance the protective effect. In order to recover the hES cells with minimal disruption, it is beneficial to use particles made of a material such as agarose that can easily be dissolved or dispersed by gentle mechanical or enzymatic action, thereby releasing the cells for harvest or further culture.

Characteristics of Undifferentiated hES Cells

Human ES cells cultured according to this invention have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES cells can be characterized by expressed cell markers detectable by antibody (flow cytometry or immunocytochemistry) or by reverse transcriptase PCR. hES cells typically have antibody-detectable SSEA-4, Tra-1-60, and Tra-1-81, but little SSEA-1, and have alkaline phosphatase activity. Panels of suitable markers detectable at the mRNA level are listed in application US 2003/0224411 A1 (Geron Corp.) Exemplary are Cripto, gastrin-releasing peptide (GRP) receptor, podocalyxin-like protein (PODXL), human telomerase reverse transcriptase (hTERT), and the POU transcription factor Oct 3/4.

As already described, an important feature of propagated hES cells is a potential to differentiate into cells of all three germ layers: endoderm, mesoderm, and ectoderm. Pluripotency of hES cells can be confirmed by forming teratomas in SCID mice, and examining them for representative tissues of all three germ layers. Alternatively, pluripotency can be determined by allowing hES cells to differentiate non-specifically (for example, by forming embryoid bodies), and then determining the cell types represented in the culture by immunocytochemistry (Example 3). Potential of hES cells to differentiate into particular cell lines can be determined according to procedures described in the next section.

Uses of Propagated hES Cells

This invention provides a method by which large numbers of pluripotent cells can be produced on a commercial scale. The cells are useful for a number of research and commercial purposes in the undifferentiated form, or can be directed to differentiate into a particular cell type.

Undifferentiated hES cells can be used to screen for factors (such as small molecule drugs, peptides, polynucleotides, and the like) or conditions (such as culture conditions or manipulation) that affect the characteristics of hES cells in culture. hES cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. Cytotoxicity or metabolic effects can be determined by cell viability, morphology, the expression or release of certain markers, receptors or enzymes, DNA synthesis or repair, and so on.

hES cells cultured according to this invention can be used to make differentiated cells of various commercially and therapeutically important tissue types.

Liver Cells

Hepatocytes can be differentiated from hES cells using an inhibitor of histone deacetylase, as described in U.S. Pat. No. 6,458,589 and PCT publication WO 01/81549 (Geron Corporation). Undifferentiated hES cells are cultured in the presence of an inhibitor of histone deacetylase.

Staged protocols for differentiating hES cells into hepatocytes are described, in US 2005/0037493 A1 (Geron Corp.). Cells are cultured with several combinations of differentiation and maturation agents in sequence, causing the hES cells to differentiate first into early endoderm or hepatocyte precursors, and then to mature hepatocyte-like cells. Briefly, differentiation into endoderm-like cells can be initiated using either butyrate, DMSO or fetal bovine serum, optionally in combination with fibroblast growth factors. Differentiation can then continue using a commercially available hepatocyte culture medium, including factors such as hepatocyte growth factor (HGF), epidermal growth factor (EGF), and/or bone morphogenic protein (e.g., BMP-2, 4, or 7) in various combinations. Final maturation may be enhanced by the presence of agents such as dexamethazone or Oncostatin M. Cells are obtained that express asialoglycoprotein, glycogen storage, cytochrome p450 enzyme expression; glucose-6-phosphatase activity, and morphological features of hepatocytes.

Nerve Cells

Neural cells can be generated from hES cells according to the method described in U.S. Pat. No. 6,833,269; Carpenter et al., Exp Neurol. 2001; 172(2):383-97; and WO 03/000868 (Geron Corporation). Undifferentiated hES cells or embryoid body cells are cultured in a medium containing one or more neurotrophins and one or more mitogens, generating a cell population in which at least ~60% of the cells express A2B5, polysialylated NCAM, or Nestin and which is capable of at least 20 doublings in culture. Exemplary mitogens are EGF, basic FGF, PDGF, and IGF-1. Exemplary neurotrophins are NT-3 and BDNF. The use of TGF-β Superfamily Antagonists, or a combination of cAMP and ascorbic acid, can be used to increase the proportion of neuronal cells that are positive for tyrosine hydroxylase, a characteristic of dopaminergic neurons. The proliferating cells can then be caused to undergo terminal differentiation by culturing with neurotrophins in the absence of mitogen.

Oligodendrocytes can be generated from hES cells by culturing them as cell aggregates, suspended in a medium containing a mitogen such as FGF, and oligodendrocyte differentiation factors such as triiodothyronine, selenium, and retinoic acid. The cells are then plated onto a solid surface, the retinoic acid is withdrawn, and the population is expanded. Terminal differentiation can be effected by plating on poly-L-lysine, and removing all growth factors. Populations can be obtained in which over 80% of the cells are positive for oligodendrocyte markers NG2 proteoglycan, A2B5, and PDGFRα, and negative for the neuronal marker NeuN. See PCT publication WO 04/007696 and Keirstead et al., J Neurosci. 2005; 25(19):4694-705.

Heart Cells

Cardiomyocytes or cardiomyocyte precursors can be generated from hES cells according to the method provided in WO 03/006950. The cells are cultured in suspension with fetal calf serum or serum replacement, and optionally a cardiotrophic factor that affects DNA-methylation, such as 5-azacytidine. Alternatively, cardiomyocyte clusters can be differentiated directly on a solid substrate using a combination of Activin A and Bone Morphogenic Protein 4: Spontaneously contracting cells can then be separated from other cells in the population, by density centrifugation.

Further process steps can include culturing the cells so as to form clusters known as cardiac bodies™, removing single cells, and then dispersing and reforming the cardiac bodies™ in successive iterations. Populations are obtained with a high proportion of cells staining positive for cTnI, cTnT, cardiac-specific myosin heavy chain (MHC), and the transcription factor Nkx2.5. See WO 03/006950, Xu et al., Circ Res. 2002; 91(6):501-8; and PCT/US2005/009081 (Geron Corporation).

Other Cell Types

Islet cells can be differentiated from hES cells by initiating differentiation of hES cells by culturing in a medium containing a combination of several factors selected from Activin A, a histone deacetylase inhibitor (such as butyrate), a mitogen (such as bFGF); and a TGF-β Superfamily antagonist (such as noggin). The cells can then be matured by culturing with nicotinamide, yielding a cell population in which at least 5% of the cells express Pdx1, insulin, glucagon, somatostatin, and pancreatic polypeptide. See WO 03/050249 (Geron Corp.).

Hematopoietic cells can be made by coculturing hES cells with murine bone marrow cells or yolk sac endothelial cells was used to generate cells with hematopoietic markers (U.S. Pat. No. 6,280,718). Hematopoietic cells can also be made by culturing hES cells with hematogenic cytokines and a bone morphogenic protein, as described in US 2003/0153082 A1 and WO 03/050251 (Roberts Institute).

Mesenchymal progenitors can be generated from hES cells according to the method described in WO 03/004605. The hES-derived mesenchymal cells can then be further differentiated into osteoblast lineage cells in a medium containing an osteogenic factor, such as bone morphogenic protein (particularly BMP-4), a ligand for a human TGF-β receptor, or a ligand for a human vitamin D receptor (WO 03/004605; Sotile et al., Cloning Stem Cells 2003; 5(2):149-55). Chondrocytes or their progenitors can be generated by culturing hES cells in microaggregates with effective combinations of differentiation factors listed in WO 03/050250 (Geron Corp.).

Other differentiation methods known in the art or subsequently developed can be applied to hES cells cultured according to this invention. hES derived cells can be used for drug screening, preparing pharmaceutical compositions, research, and many other worthwhile purposes.

Commercial Distribution

Components of the culture system of this invention may be offered for sale, sold, or otherwise distributed from the place of manufacture for use by another entity for any purpose. Components may also be sold or distributed together in various useful combinations, such as two or more of the following:

- media suitable for culturing hES cells in suspension factors
- extracellular matrix components or thickeners present in or to be added to the medium
- microcarriers present in or to be added to the medium
- vessels adapted for suspension culture
- the hES cells themselves, either growing in the culture system, or stored in another form, but intended for use in the culture system The products and product combinations are packaged in suitable containers, optionally in kit form, and may be accompanied by written information on the use of the materials according to this invention—such as maintaining or expanding hES cells. The information may be written in any language on any communication medium accessible and understandable by the intended user. It may take the form of a label on the container or the kit, or a product insert packaged with the container and distributed together. Equivalent forms are descriptions, instructions, or explanations written in hard copy or in electronic form available to the user or the intended user as reference or resource material associated with the commercially distributed product.

The examples that follow are illustrations not meant to limit the claimed invention

EXAMPLES

Example 1: Growing Pluripotent Stem Cells in Rapid Expansion Medium

A line of hES cells was obtained that had originally been grown on mouse embryonic fibroblast feeder cells, and then expanded for 20 passages in a feeder-free environment comprising Matrigel® extracellular matrix and conditioned medium, according to U.S. Pat. No. 6,800,480; as elaborated in Xu et al., Stem Cells 2005; 23(3):315-23.

The hES cells were next weaned onto X-VIVO™ 10 expansion medium from Biowhittaker; or QBSF™-60 from Quality Biological Inc. For use in these experiments, the X-VIVO™ 10 medium was supplemented with the usual goodies: namely, 2 mM L-glutamine, 1% non-essential amino acids (Gibco), 0.1 mM β-mercaptoethanol, and 8 ng/mL bFGF. The medium was further supplemented with 8 ng/mL or 40 ng/mL of bFGF (Gibco); 40 ng/mL of bFGF and 15 ng/mL of SCF (R & D System); or 40 ng/mL of bFGF and 75 ng/mL of Flt3 ligand (R & D System). QBSF™-60 medium was supplemented with 0.1 mM β-mercaptoethanol, 1% non-essential amino acids (Gibco) and 40 ng/mL of bFGF. hES cells cultured in mEF conditioned medium were used as control in these experiments.

The hES cells were first passaged onto Matrigel® coated plates using collagenase IV, and cultured for 2 days with conditioned medium. On day 2, the conditioned medium was replaced with 80% unconditioned ES medium plus 20% expansion medium. Cells were fed fresh daily and passaged weekly. The proportion of expansion medium was increased by 20% approximately every 2 days until the cells were completely weaned, and then grown until they had been passaged 6 more times.

Figure 1:
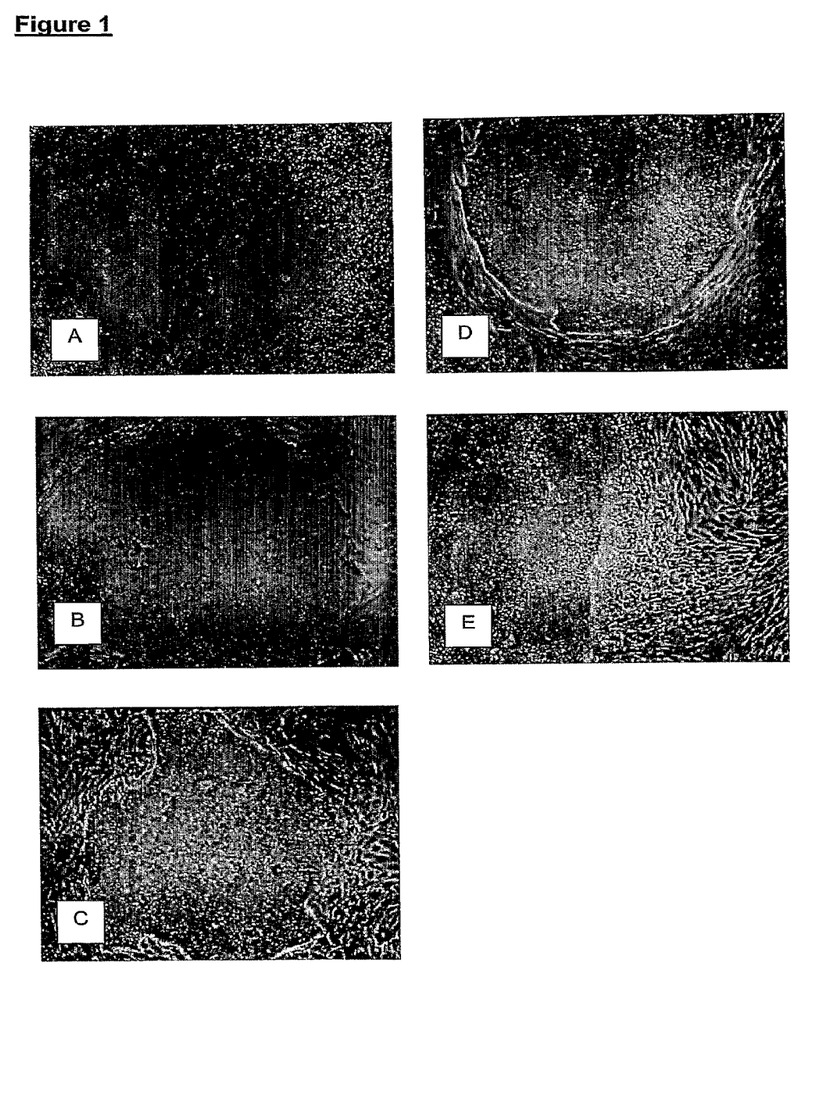
FIG. 1 shows colonies of hES cells after six passages on a solid surface in unconditioned medium supplemented with growth factors. (A) mEF conditioned ES medium (control)+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL). All three base media (ES medium, X-VIVO™ 10, and QBSF™-60) can be used to expand hES cells in feeder-free culture. In this illustration, the cells growing in combination shown in (C) expanded 8.2-fold per passage, whereas those in conditioned medium expanded 2.2-fold.

FIG. 1 shows colonies of hES cell at the end of 6 passages (sufficient for full adaptation) in the following media: (A) mEF conditioned medium+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL).

The following table shows the average total cell expansion per passage, for undifferentiated hES cells cultured for 4 passages in mEF conditioned medium, or for 7 passages in X-VIVO™ 10 or QBSF™-60.

TABLE 1

Growth Rates for ES Cell Cultures

| Medium | Average Cell Expansion per Passage |
| --- | --- |
| mEF conditioned medium | 2.2 fold |
| X-VIVO ™ 10 + bFGF (40 ng/mL) | 6.0 fold |
| X-VIVO ™ 10 + bFGF (40 ng/mL) + SCF (15 ng/mL) | 8.2 fold |
| X-VIVO ™ 10 + bFGF (40 ng/mL) + Flt3 ligand (75 ng/mL) | 5.0 fold |
| QBSF ™-60 + bFGF (40 ng/mL) | 6.4 fold |

The average expansion of cells per passage in X-VIVO™ 10 and QBSF™-60 was greater than the cells cultured in mEF conditioned medium culture. The cells in mEF conditioned medium were passaged on average every 7 days, while the cells in X-VIVO™ 10 and QBSF™-60 were passaged on average every 5 days. Thus, the rate of expansion in unconditioned X-VIVO™ 10 or QBSF™-60 was ~3.2 to 5.2 times faster than in mEF conditioned ES medium.

Figure 2:
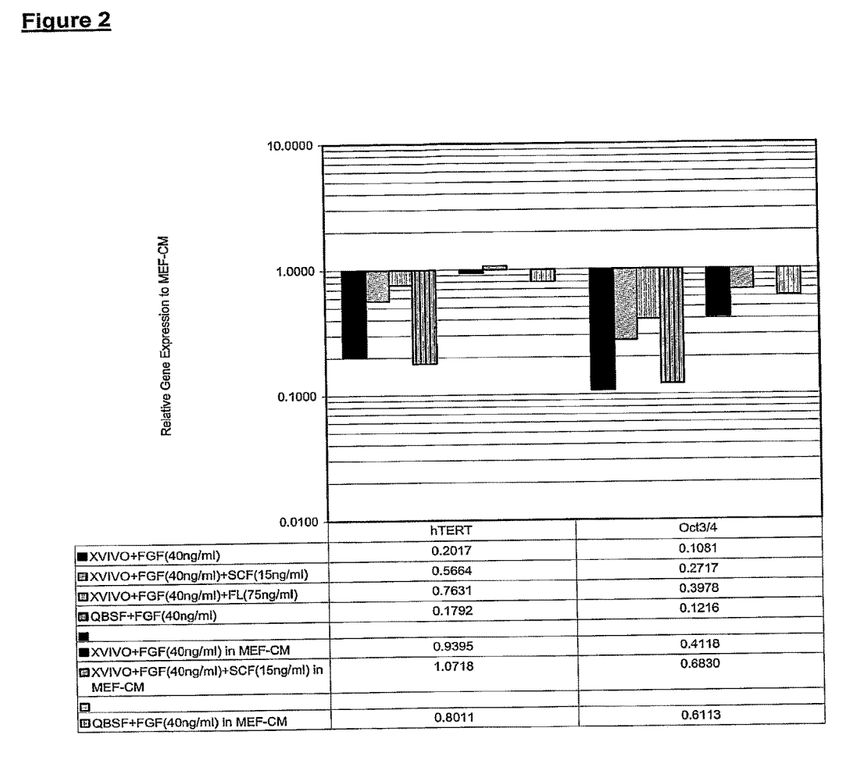
FIG. 2 shows the gene expression profile of hTERT and Oct3/4, measured by real time RT-PCR, as described in Example 1.

FIG. 2 shows the gene expression profile of hTERT and Oct3/4. The RNA was isolated from the cells using High Pure RNA Isolation Kit (Roche Diagnostics) and evaluated by Taqman™ assay (real time RT-PCR). The gene expression in each of the test condition is plotted relative to expression in the control culture. Taking into consideration the instrument error and assay variability, differences in expression between the test and control samples are only significant if greater than 2-fold. The analysis shows expression of hTERT and Oct-3/4 decreases somewhat upon adaptation to unconditioned X-VIVO™ 10 or QBSF™-60 medium (first four bars in each set), but returns to standard levels when the cells are passaged back into mEF conditioned medium (last three bars in each set).

To confirm that cells cultured in unconditioned medium retain their pluripotency, embryoid bodies were formed and analyzed by immunocytochemistry for phenotypic markers representing each of the three germ layers. After passage 7 in expansion medium, the cells were dissociated into small clumps using 200 U/mL collagenase IV at 37'C for 10 min, placed in suspension culture in differentiation medium (DMEM+10% FBS) for 4 days, then transferred onto poly-L-ornithine hydrobromide coated plates for a further 10 days. They were fixed in 4% paraformaldehyde, permeabilized, and labeled by immunocytochemistry.

Figure 3:
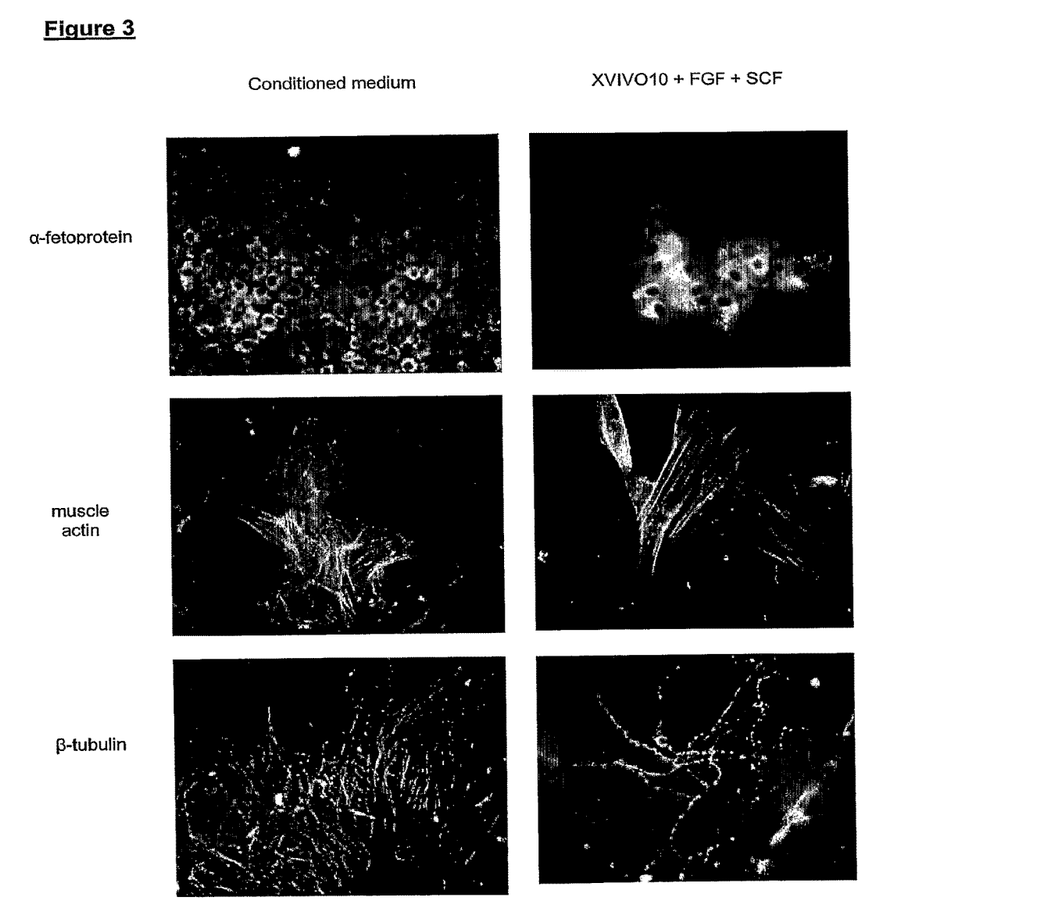
FIG. 3 demonstrates that cells cultured in unconditioned medium retain their pluripotency. hES cells passaged 7 times in mEF conditioned medium, or unconditioned X-VIVO™ 10 medium containing bFGF and SCF. The cells were then differentiated into embryoid bodies, plated, and analyzed by immunocytochemistry for phenotypic markers representing each of the three germ layers. The cells stain for α-fetoprotein (representing endoderm); muscle actin (representing mesoderm), and β-tubulin III (representing ectoderm).

FIG. 3 shows the results. hES cells passaged 7 times in unconditioned X-VIVO™ 10 medium stained for α-fetoprotein (representing endoderm); muscle actin (representing mesoderm), and β-tubulin III (representing ectoderm).

Thus, hES cells can be expanded in fresh (non-conditioned) media in a feeder-free environment at a rapid rate suitable for commercial production—as much as 2- to 5-fold faster or more compared with growth in conditioned medium or on feeder cells. The cells retain the morphology of undifferentiated hES cells, and can be differentiated into derivative cells representing all three germ layers.

Example 2: Culture of hES Cells in a Defined System Free of Animal-Based Products hES cells cultured in MEF-CM on Matrigel® were passaged to a fresh (non-conditioned) serum free medium: X-VIVO™ 10 supplemented with Glutamine, non-essential amino acids and β-mercaptoethanol, plus 80 ng/mL human basic FGF on Matrigel®, and then adapted to surfaces coated with human laminin. Alternatively, cryopreserved cells were directly thawed into the same medium containing 80 ng/mL hbFGF. The cells were passaged every 5-6 days using Collagenase IV.

Cultures grown under these conditions were similar or better than cultures on Matrigel®. (A) morphology for cells grown in mEF conditioned medium; (B) morphology fin defined medium on laminin; (C) Surface marker SSEA-4 expression in mEF-CM (H1p62) or defined medium (H1p34+28); (D) Expression of surface marker Tra-1-60 in mEF-CM or defined medium. Culture performance in the defined medium on laminin was superior: very large ES cell colonies were observed, with colonies representing about 80% of the culture. Levels of marker expression were as follows:

TABLE 2

Marker Expression in Defined Culture Conditions

| Passage no. | Culture medium | Surface marker expression | | Relative gene expression | | |
|---|---|---|---|---|---|---|
| | | SSEA-4 | Tra-1-60 | hTERT | Oct3/4 | Cripto |
| Experiment 1: | | | | | | |
| H1p41 | Conditioned | 79% | 93% | 1.00 | 1.00 | 1.00 |
| H1p31 + 10 | Defined | 92% | 87% | 2.85 ± 0.58* | 0.74 ± 0.04 | 1.82 ± 0.62 |
| Experiment 2: | | | | | | |
| H1p44 | Conditioned | 81% | 91% | 1.00 | 1.00 | 1.00 |
| H1p34 + 11 | Defined | 77% | 84% | 1.11 ± 0.38 | 0.57 ± 0.24 | 0.76 ± 0.39 |
| Experiment 3: | | | | | | |
| H1p47 | Conditioned | 78% | 92% | 1.00 | 1.00 | 1.00 |
| H1p35 + 12 | Defined | 80% | 86% | 2.00 ± 0.15 | 0.86 ± 0.20 | 3.12 ± 0.91 |

*mean ± SD for 3 RT-PCR determinations

Expression of other markers characteristic of undifferentiated hES cells was also comparable: Measured by real-time PCR, the levels of hTERT and Cripto were the same or greater in defined medium compared with mEF-CM, while the expression of Oct 3/4 was lower by about 28% (average of three experiments). TRAP analysis showed that the cells retained telomerase enzyme activity.

Cells grown in completely defined culture system at p34+11 (75 days) were harvested and used to make teratomas in SCID mice to evaluate pluripotency. The teratomas showed evidence for pigmented epithelium (endoderm); renal tissue (endoderm); mesenchymal tissue (mesoderm); and neural tubes (ectoderm). This confirms that the cells retained their pluripotency.

Example 3: Culturing hES Cells in Suspension

With a view to increasing the yield of hES cells per culture volume, the cells were cultured in suspension, and then evaluated for morphology and their ability to form differentiated cells representative of all three germ layers.

H9 hES cells grown on Matrigel® were harvested from 6-well plates and seeded into a spinner flask under the following condition
 Vessel: 100 mL spinner flask
 Inoculation (seeding) density: 3.6×10$^5$ cells/mL;
 Medium volume: 50 mL per spinner flask
 Medium used: mEF conditioned medium containing bFGF (8 ng/mL)
 Agitation rate: 20 rpm (Bellco carrier magnetic stirrer)
 Atmosphere: 37° C. CO2 incubator
 Medium exchange: Every other day (exchanged by letting the cells settle down and replacing the supernatant)
H9 hES cells were maintained in the spinner flask under these conditions for 6 days.

Figure 4:
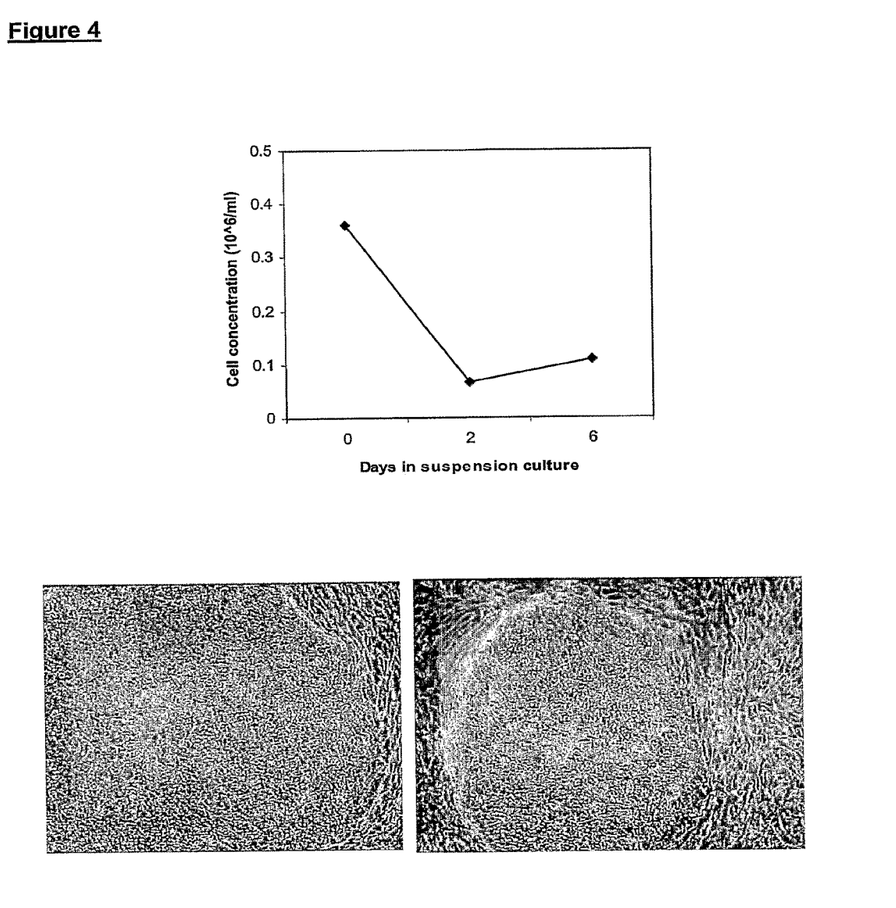
FIG. 4 shows the cell count of hES cells grown in suspension culture in spinner flasks (Example 3). After the culture became established, the cells continued to thrive at the same density (Upper Panel). When passaged back to standard surface culture they reverted to typical morphology of the undifferentiated phenotype: namely, distinct colonies of cells having the classic hES cell morphology (Lower Panel).

FIG. 4 (upper panel) shows the results. Following an initial decline during which the culture was established, the cell number began to rise from day 2 through day 6.

At this point, the cells were plated back into a 6-well plate coated with Matrigel® to determine whether they still had the phenotype of undifferentiated cells. The culture continued using mEF-CM medium containing bFGF (8 ng/mL).

FIG. 4 (lower panel) shows the results. After a single passage, the cells grew and exhibited morphology of undifferentiated cells.

Pluripotency of the cells was evaluated by forming embryoid bodies. The cells were harvested from confluent culture using Collagenase IV, and transferred to a low attachment 6-well plate in DMEM+20% FBS. EBs were formed and maintained for four days. The EBs were then replated onto polyornithine-coated chamber slides. After a further 11 days, the EB outgrowths were stained for α-fetoprotein (endoderm), muscle actin (mesoderm) and β-tubulin with neuron morphology (ectoderm).

Figure 5:
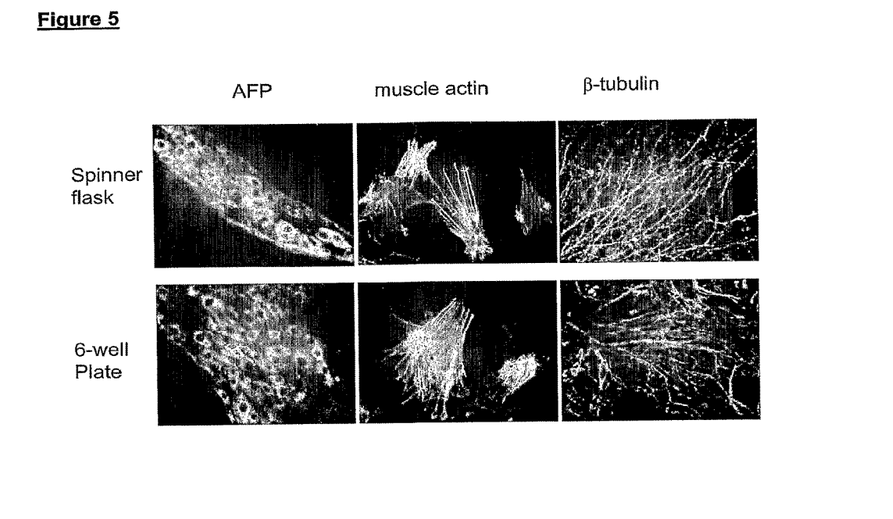
FIG. 5 is taken from an experiment in which the cells grown in suspension (FIG. 4) were differentiated into embryoid bodies, plated, and then analyzed by immunocytochemistry for specific cell types (Top Row). Cells maintained throughout by standard surface culture are also shown (Bottom Row). The cells cultured in suspension maintained full pluripotency, demonstrating the effectiveness of the suspension culture system in maintaining the important properties of undifferentiated hES cells.

FIG. 5 shows the results. The top row shows cells differentiated from the hES cells maintained in suspension culture, and then plated back onto laminin under standard conditions. The lower row shows cells differentiated from the same hES cell line that were maintained throughout as plated cells. As shown in these images, hES cells maintained in suspension maintained their full capacity to differentiate into derivatives of all three-germ layers.

Figure 6:
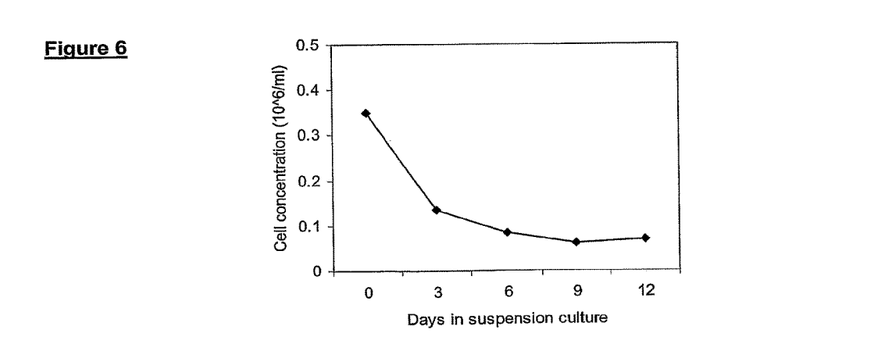
FIG. 6 shows the cell count of another suspension culture in spinner flasks.

In another experiment, H9 hES cells were cultured under the following conditions:
 Vessel: 100 mL spinner flask
 Inoculation (seeding) density: 3.5×10$^5$ cells/mL
 Medium volume: 50 mL per spinner flask
 Medium used: mEF-CM+bFGF (8 ng/mL)
 Agitation rate: 20 rpm (as before)
 Medium exchange: Once every three days FIG. 6 shows the results. Once the culture was established, the cells were maintained happily for the full 12 day period.

Example 4: Long-Term Suspension Culture

This experiment was done with another hES cell line. The cells were cultured using a shaker flask instead of a spinner flask under several different culture conditions, and the culture was extended for over two months.

H1 hES cells were harvested from 6-well plates (growing on Matrigel® in mEF conditioned medium) and seeded into shaker flasks under the following conditions:
 Vessel: 100 mL Shaker Flask
 Inoculation (seeding) density: 5.0×10$^5$ cells/mL
 Medium volume: 15 mL per shaker flask
 Agitation rate: 80 rpm (Labline rotator/shaker in a 37° C. CO$_2$ incubator)
 Medium exchange: Every other day initially, once every 2-3 days later The media used and culture periods were as follows:
- A: mEF-CM+bFGF (8 ng/mL). Maintained for 98 days.
- B: mEF-CM+bFGF (8 ng/mL)+laminin (33 μg/mL to begin with, ~10 μg/mL thereafter for the rest of the culture). Maintained for 49 days.
- C: X-VIVO™ 10+FGF (40 ng/mL)+Flt-3 (75 ng/mL). Maintained for 11 days.
- D: X-VIVO™ 10+FGF (40 ng/mL)+Flt-3 (75 ng/mL)+ laminin (33 μg/mL to begin with, ~10 μg/mL thereafter for the rest of the culture). Maintained for 11 days.

Cell counts over the period of the culture are shown in the following Table.

TABLE 3

Growth of hES Cells in Suspension Cultures

| Days in culture | Medium A ($10^5$ cells/mL) | Medium B ($10^5$ cells/mL) | Medium C ($10^5$ cells/mL) | Medium D ($10^5$ cells/mL) |
|---|---|---|---|---|
| 0 | 5.0 | 5.0 | 5.0 | 5.0 |
| 1 | (not counted) | 7.5 | 6.9 | 7.3 |
| 3 | 5.9 | 5.0 | 2.8 | 2.8 |
| 11 | 2.7 | 2.3 | 2.5 | 2.4 |
| 32 | 0.3 | 0.15 | — | — |
| 98 | 14 | — | — | — |

To determine whether the cells were maintaining the undifferentiated phenotype, cells cultured for 4 weeks in Medium A were plated back onto Matrigel® in mEF conditioned medium containing bFGF.

Figure 7:
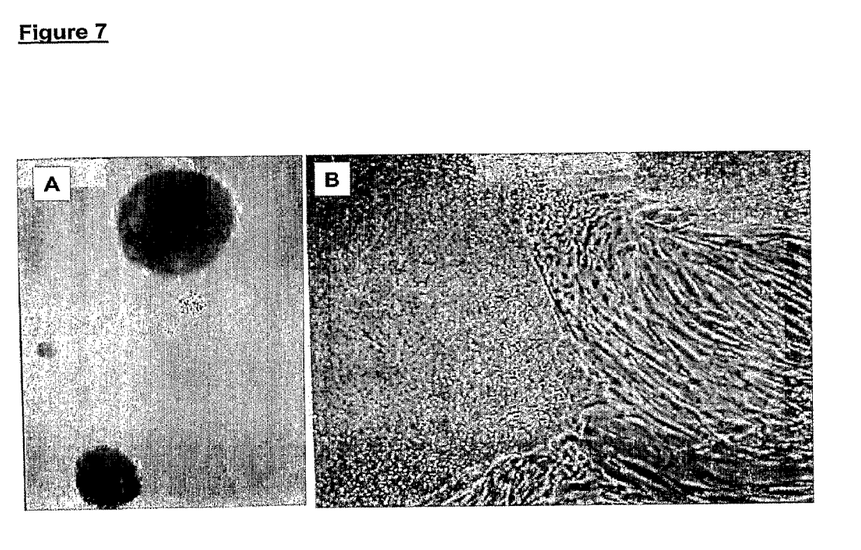
FIG. 7 shows cells from a different hES cell line maintained in suspension culture on a shaker device. After four weeks, the cells were plated back onto a solid surface, and showed classic undifferentiated hES cell morphology, as shown here. A culture was continued in this fashion for over three months, showing substantial proliferation of the cells in suspension.

FIG. 7 shows the results. After passaging, the cells derived from the suspension culture were shown to grow and exhibit characteristic undifferentiated hES cell colonies.

These data indicate that hES cells can be maintained in suspension culture for at least three months, potentially undergoing expansion by 3- to 40-fold after the culture becomes fully established.

Example 5: Suspension Cultures Using Fresh Medium

The next experiment evaluates alternative additives for use with fresh (unconditioned) medium in suspension cultures.

hES cells are harvested from a surface culture in fresh medium under standard conditions (substrate of human laminin from Sigma, coated onto 6-well plates at 2 μg/cm²; X-VIVO 10™ medium containing 80 ng/mL bFGF and 0.5 ng/mL TGFβ1). The harvested cells are passaged into suspension culture in 100 mL spinner flasks, using 50 mL per flask at an initial density of ~5×10⁵ cells/mL. The following medium alternatives are evaluated:
1) X-VIVO™ 10+bFGF (80 ng/mL)
2) X-VIVO™ 10+bFGF (80 ng/mL)+TGFβ1 (0.5 ng/mL)
3) X-VIVO™ 10+bFGF (40 ng/mL)+TGFβ1 (0.5 ng/mL)
4) X-VIVO™ 10+bFGF (80 ng/mL)+TGFβ1 (0.5 ng/mL)+10 μg/mL human laminin
5) X-VIVO™ 10+bFGF (80 ng/mL)+TGFβ1 (0.5 ng/mL)+50 μg/mL human serum albumin Each spinner flask is placed on a Belico carrier magnetic stirrer (Belico Biotechnology, Vineland N.J.) in a 37° C. $CO_2$ incubator, at an initial agitation rate to 20 rpm. The agitation rate is adjusted to keep the cells in suspension and provide sufficient aeration, while minimizing shear forces. Medium is changed every 2-3 days as before, monitoring cell count, and the flasks are split as needed.

At regular intervals, cells are sampled from each flask and plated back onto a laminin coated surface to evaluate morphology. Cells returned to surface cultures and cells taken directly from the suspension cultures are tested for pluripotency by immunocytochemical staining of EB derived cells, as in Example 3

The compositions and procedures described above can be effectively modified without departing from the claimed invention and its equivalents.

The invention claimed is:

1. A method for culturing undifferentiated human pluripotent stem (hPS) cells in suspension, the method comprising:
   a) suspending undifferentiated hPS cells in a cell culture medium comprising basic fibroblast growth factor (bFGF);
   b) maintaining the hPS cells substantially undifferentiated while culturing in suspension;
   c) changing the cell culture medium periodically; and
   d) optionally splitting the culture from time to time, so as to reduce the density of the hPS cells in culture;
   wherein the hPS cells are not grown attached to a solid substrate.

2. The method of claim 1, wherein the concentration of bFGF is at least 40 ng/mL.

3. The method of claim 1, wherein the concentration of bFGF is about 40 ng/mL.

4. The method of claim 1, wherein the concentration of bFGF is about 80 ng/mL.

5. The method of claim 1, wherein the cell culture medium further comprises at least one factor selected from transforming growth factor beta (TGF β), stem cell factor (SCF), and Flt3 ligand (Flt3L).

6. The method of claim 1, wherein the hPS cells are cultured in suspension for a period of at least two months.

7. The method of claim 1, further comprising plating the undifferentiated hPS cells onto a solid substrate and continuing to culture the hPS cells in a substantially undifferentiated state.

8. The method of claim 1, further comprising harvesting the undifferentiated hPS cells from the culture and differentiating them.

9. The method of claim 7, further comprising differentiating the plated hPS cells.

10. The method of claim 1, wherein the undifferentiated hPS cells are cultured in suspension inside a cell culture vessel that is being agitated, rocked, or spun.

11. The method of claim 1, wherein the undifferentiated hPS cells are cultured in suspension inside a cell culture vessel selected from a spinner flask, shaker flask, a fermentor and a bioreactor.

* * * * *